United States Patent
Oonuma et al.

(10) Patent No.: US 7,451,665 B2
(45) Date of Patent: Nov. 18, 2008

(54) AUTOANALYZER AND PROBE CLEANING METHOD

(75) Inventors: Takehiko Oonuma, Sakura (JP); Hiroko Takayama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/668,246

(22) Filed: Jan. 29, 2007

(65) Prior Publication Data
US 2007/0175284 A1 Aug. 2, 2007

(30) Foreign Application Priority Data
Jan. 30, 2006 (JP) ............................. 2006-021272

(51) Int. Cl.
*G01N 1/00* (2006.01)
(52) U.S. Cl. .................................................. 73/864.25
(58) Field of Classification Search ................... None
See application file for complete search history.

(56) References Cited

U.S. PATENT DOCUMENTS

| 4,971,913 | A | 11/1990 | Manabe et al. | |
|---|---|---|---|---|
| 5,289,385 | A | 2/1994 | Grandone | |
| 2004/0175833 | A1* | 9/2004 | Tatsumi | 436/49 |
| 2005/0014274 | A1 | 1/2005 | Lee et al. | |
| 2006/0263250 | A1* | 11/2006 | Blouin et al. | 422/63 |

FOREIGN PATENT DOCUMENTS

| DE | 43 14 180 A1 | 11/1993 |
|---|---|---|
| JP | 4-169851 | 6/1992 |
| JP | 2004-251797 | 9/2004 |
| WO | WO 01/65266 A1 | 9/2001 |
| WO | WO 2007/086477 A1 | 2/2007 |

* cited by examiner

*Primary Examiner*—Robert R Raevis
(74) *Attorney, Agent, or Firm*—Oblon, Spivak, McClelland, Maier & Neustadt, P.C.

(57) ABSTRACT

A specimen is sequentially sampled by a probe, and at least one of the number of times of cleaning and a cleaning time when cleaning the probe is changed based on at least one of the number of times of sampling of the specimen by the probe and a sampling amount of the specimen.

9 Claims, 7 Drawing Sheets

AUTOANALYZER AND PROBE CLEANING METHOD

CROSS-REFERENCE TO RELATED APPLICATIONS

This application is based upon and claims the benefit of priority from prior Japanese Patent Application No. 2006-021272, filed Jan. 30, 2006, the entire contents of which are incorporated herein by reference.

BACKGROUND OF THE INVENTION

1. Field of the Invention

The present invention relates to an improvement in an autoanalyzer that samples a specimen by using a probe to perform biochemical analysis and immunological analysis with respect to the specimen, and in a probe cleaning method of cleaning the probe used in the autoanalyzer.

2. Description of the Related Art

An autoanalyzer is provided in, e.g., hospitals. The autoanalyzer analyzes a specimen, e.g., blood or urine in accordance with each inspection item. The autoanalyzer is constituted by coupling a biochemical analysis unit that performs biochemical analysis with respect to a specimen and an immunological analysis unit that carries out immunological analysis. The autoanalyzer accommodates a specimen in a specimen container, and carries this specimen container between the biochemical analysis unit and the immunological analysis unit by using a carriage system.

A reaction tube is provided in each of the biochemical analysis unit and the immunological analysis unit. The reaction tube is carried by the carriage system. When the reaction tube is carried to the biochemical analysis unit or the immunological analysis unit, the specimen in the specimen container is divided and poured into the reaction tube in each of the biochemical analysis unit and the immunological analysis unit. Divided pouring is carried out by each sampling mechanism provided in each of the biochemical analysis unit and the immunological analysis unit. Each sampling mechanism is constituted by, e.g., providing a sampling probe to a sampling arm. The sampling mechanism immerses the sampling probe in the specimen in the specimen container by driving the sampling arm, sucks the specimen in the specimen container by the sampling probe, moves the sampling probe into the reaction tube, and discharges the specimen into the reaction tube from the sampling probe.

The autoanalyzer sequentially carries the plurality of specimen containers accommodating different specimens therein to the biochemical analysis unit and the immunological analysis unit to divide and pour the specimens into the respective reaction tubes. Therefore, as shown in FIG. 15, the sampling probe is cleaned to avoid contamination between the previous specimen and the next specimen, i.e., carry-over. The sampling probe is cleaned after the specimen is sucked to be discharged into the reaction tube. As a result, in regard to an amount of a residue of the sampling probe, an amount Cb of the residue after cleaning is smaller than an amount Ca of the residue before cleaning as shown in FIG. 15.

As a technology concerning cleaning the sampling probe, there is one disclosed in, e.g., Jpn. Pat. Appln. KOKAI Publication No. 2004-251797. Jpn. Pat. Appln. KOKAI Publication No. 2004-251797 discloses forming an opening, from which a cleaning liquid is discharged, to include a region where the cleaning liquid discharged toward an outer wall of a sampling probe placed in a cleaned state is immersed in a specimen.

The biochemical analysis unit and the immunological analysis unit have a considerable difference in measurement sensitivity with respect to a specimen. The sensitivity of the immunological analysis unit is higher than that of the biochemical analysis unit. As a result, the biochemical analysis unit does not require high performance in relation to carry-over between specimens. Even if there is carry-over between the previous specimen and the next specimen, the biochemical analysis unit does not affect an analysis result.

On the other hand, the immunological analysis unit requires high performance concerning carry-over between specimens. Therefore, if there is carry-over between the previous specimen and the next specimen, an error in an analysis result occurs in the immunological analysis unit.

Carry-over between specimens is also dependent on a degree of contamination of a sampling probe, conditions under which a specimen is sampled, and others. Therefore, in the existing circumstances, it is difficult to keep the performance requiring the carry-out performance between specimens under all conditions.

It has been confirmed from experiments that the carry-over between specimens vary depending on sampling conditions due to the following tendency. When the number of times of sampling is increased, the carry-over between specimens is also increased. An increase in the number of times of sampling and an increase in the carry-over do not necessarily have a proportionality relation. The carry-over between specimens is increased in accordance with an integration amount of specimens to be sucked by a sampling probe. Here, the integration amount of specimens is a sum total of sampling amounts of all specimens including a dummy and sampling amounts of the first sampling to the nth sampling, for example.

A maximum number of times of sampling in the autoanalyzer exceeds 100 times because of specifications. A sampling probe may suck and discharge a specimen having a sampling amount of, e.g., 35 µL because of its specifications. In such sampling, even if the number of times of sampling is the same as that of sampling having an average sampling amount, e.g., approximately 4 µL, the carry-over between specimens becomes large.

Under two types of sampling conditions, i.e., the number of times of sampling and a sampling amount, a value of the carry-over between specimens required under maximum conditions in specifications is, e.g., 0.1 ppm or below. However, it is difficult to set the value of the carry-over to, e.g., 0.1 ppm or below.

It is an object of the present invention to provide an autoanalyzer that can assure performance requiring carry-over between specimens even if the number of times of sampling or a sampling integration amount of the specimens is increased, and a probe cleaning method.

BRIEF SUMMARY OF THE INVENTION

According to a first aspect of the present invention, there is provided an autoanalyzer comprising: a probe that samples a specimen; an analysis unit that analyzes the specimen sampled by the probe; a cleaning mechanism that cleans the probe; and a probe cleaning change section that changes at least one of the number of times of cleaning and a cleaning time of the probe by the cleaning mechanism based on at least one of the number of times of sampling of the specimen and a sampling amount of the specimen by the probe.

According to a second aspect of the present invention, there is provided a probe cleaning method comprising: sequentially sampling a specimen by a probe; and changing at least one of the number of times of cleaning and a cleaning time when cleaning the probe based on at least one of the number of times of sampling of the specimen by the probe and a sampling amount of the specimen.

DETAILED DESCRIPTION OF THE INVENTION

A first embodiment according to the present invention will now be explained hereinafter with reference to the accompanying drawings.

Figure 1:
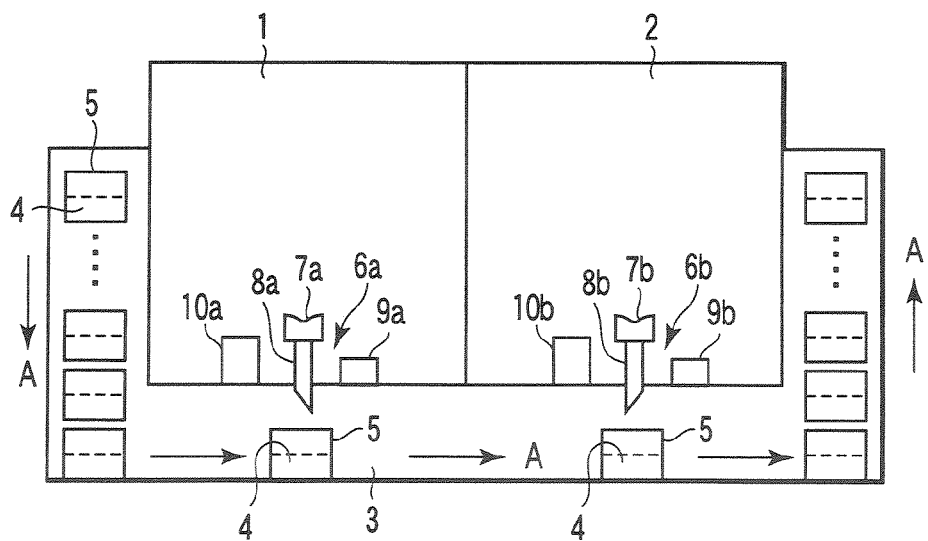
FIG. 1 is a structural view showing a first embodiment of an autoanalyzer according to the present invention.

FIG. 1 is a structural view of an autoanalyzer. The autoanalyzer is constituted by coupling a biochemical analysis unit 1 with an immunological analysis unit 2 and providing a carriage unit 3 between the biochemical analysis unit 1 and the immunological analysis unit 2. The carriage unit 3 carries a plurality of specimen containers 5 accommodating each specimen 4, e.g., a blood serum or urine therein from the biochemical analysis unit 1 to the immunological analysis unit 2 in a direction indicated by arrows A. The respective specimens 4 accommodated in the respective specimen containers 5 are taken from different patients.

A sampling mechanism 6a is provided in the biochemical analysis unit 1. The sampling mechanism 6a divides and pours the specimen 4 accommodated in the specimen container 5 into the biochemical analysis unit 1. Specifically, the sampling mechanism 6a is constituted by providing a sampling probe 8a at a distal end of a sampling arm 7a. A reaction container 9a is provided in the biochemical analysis unit 1.

The sampling mechanism 6a moves the sampling arm 7a to a position above the specimen container 5, moves down the sampling probe 8a to be immersed in the specimen 4 in the specimen container 5, sucks the specimen 4, moves up the sampling probe 8a, moves the sampling probe 8a to a position above the reaction container 9a, and moves down the sampling probe 8a to discharge the specimen 4 into the reaction container 9a. The biochemical analysis unit 1 performs biochemical analysis of the specimen 4 divided and poured into the reaction container 9a.

A sampling mechanism 6b is provided in the immunological analysis unit 2. The sampling mechanism 6b divides and pours the specimen 4 accommodated in the specimen container 5 into the immunological analysis unit 4. Specifically, the sampling mechanism 6b is constituted by providing a sampling probe 8b at a distal end of a sampling arm 7b. A reaction container 9b is provided in the immunological analysis unit 2. The sampling mechanism 6b moves the sampling arm 7b to a position above the specimen container 5, moves down the sampling probe 8b to be immersed in the specimen 4 in the specimen container 5, sucks the specimen 4, moves up the sampling probe 8b, moves the sampling probe 8b to a position above the reaction container 9b, and moves down the sampling probe 8b to discharge the specimen 4 into the reaction container 9b. The immunological analysis unit 2 performs immunological analysis of the specimen 4 divided and poured into the reaction container 9b.

The biochemical analysis unit 1 and the immunological analysis unit 2 have a difference corresponding to a measurement sensitivity with respect to the specimen 4, and a sensitivity of the immunological analysis unit 2 is higher than that of the biochemical analysis unit 1.

Figure 2:
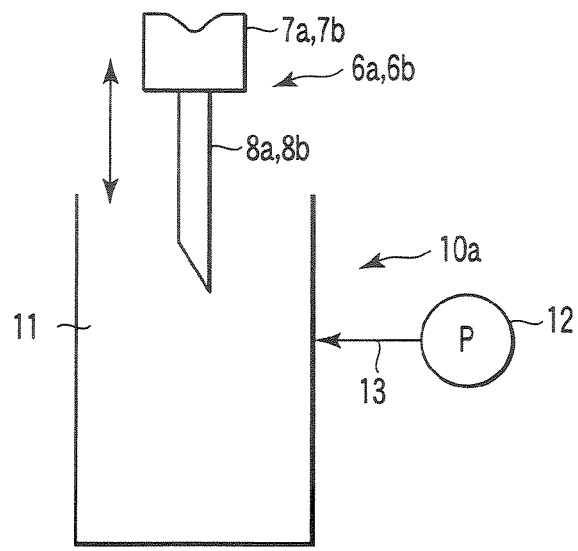
FIG. 2 is a structural view showing a cleaning mechanism in the autoanalyzer.

The biochemical analysis unit 1 and the immunological analysis unit 2 respectively have cleaning mechanisms 10a and 10b. The respective cleaning mechanisms 10a and 10b clean the respective sampling probes 8a and 8b. FIG. 2 is a structural view of each cleaning mechanism 10a or 10b. Each cleaning mechanism 10a or 10b is constituted by providing a cleaning pump 12 to a cleaning tank 11. The cleaning mechanism 10a drives the cleaning pump 12 with respect to the sampling probe 8a or 8b inserted into the cleaning tank 11 to inject a cleaning liquid 13, thereby cleaning the sampling probe 8a or 8b.

A timing of cleaning each sampling probe 8a or 8b is as follows. The sampling probe 8a will be explained. The sampling mechanism 6a moves the sampling probe 8a to, e.g., a position above the specimen container 5 from an installation position of the cleaning mechanism 10a, moves down the sampling probe 8a to be immersed in the specimen 4 in the specimen container 5, sucks the specimen 4, moves up the sampling probe 8a, moves the sampling probe 8a to a position above the reaction container 9a, and moves down the sampling probe 8a to discharge the specimen 4 into the reaction container 9a.

Then, the sampling mechanism 6a moves the sampling arm 7a to the installation position of the cleaning mechanism 10a. Here, the cleaning mechanism 10a cleans the sampling probe 8a.

The sampling mechanism 6a again moves the sampling arm 7a to the position above the specimen container 5, and immerses the sampling probe 8a in the specimen 4 in the specimen container 5 to suck the specimen 4.

The sampling mechanism 6a moves the sampling probe 8a from, e.g., the installation position of the cleaning mechanism 10a to an installation position of the specimen container 5, immerses the sampling probe 8a in the specimen 4 in the specimen container 5, sucks the specimen 4, discharges the sucked specimen 4 into the reaction container 9a, and cleans the sampling arm 7a in the cleaning mechanism 10a. This operation is determined as one cycle.

Figure 3:
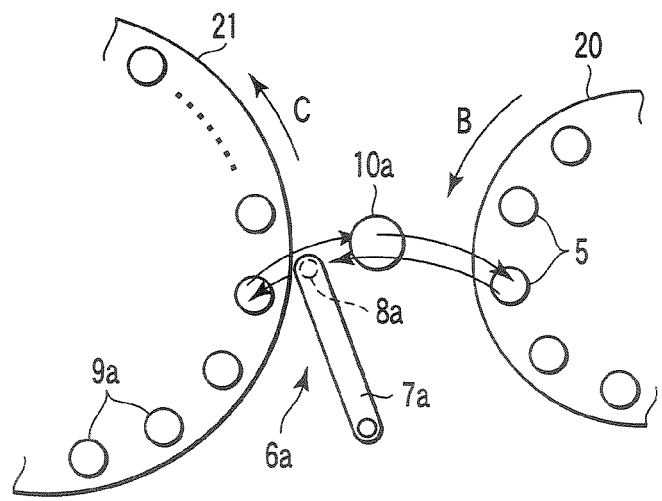
FIG. 3 is a view showing another structure in the autoanalyzer.

Each of the biochemical analysis unit 1 and the immunological analysis unit 2 sucks the specimen 4 in the specimen container 5 carried by the carriage unit 3 by using each sampling mechanism 6a or 6b, and discharges the specimen 4 into each reaction container 9a or 9b. The present invention is not restricted to this structure, and each of the biochemical analysis unit 1 and the immunological analysis unit 2 may have a structure shown in FIG. 3. The plurality of specimen containers 5 are provided in a disc sampler 20. This disc sampler 20 rotates in, e.g., a direction indicated by an arrow B. The plurality of reaction containers 9a are provided in a reaction disc 21. This reaction disc 21 rotates in, e.g., a direction indicated by an arrow C. The sampling mechanism 6a is provided between the disc sampler 20 and the reaction disc 21. The cleaning mechanism 10a is provided in a movement path of the sampling probe 8a between the disc sampler 20 and the reaction disc 21.

One cycle operation of the sampling mechanism 6a is as follows. The sampling mechanism 6a moves the sampling probe 8a from, e.g., an installation position of the cleaning mechanism 10a to a position above the specimen container 5, moves down the sampling probe 8a to be immersed in the specimen 4 in the specimen container 5, sucks the specimen 4, moves up the sampling probe 8a, rotates and moves the sampling probe 8a to a position above the reaction container 9a, and moves down the sampling probe 8a to discharge the specimen 4 into the reaction container 9a.

Then, the sampling mechanism 6a moves the sampling arm 7a to the installation position of the cleaning mechanism 10a. Here, the cleaning mechanism 10a cleans the sampling probe 8a.

The sampling mechanism 6a again moves the sampling arm 7a to the position above the specimen container 5, and immerses the sampling probe 8a in the specimen 4 in the specimen container 5 to suck the specimen 4.

Figure 4:
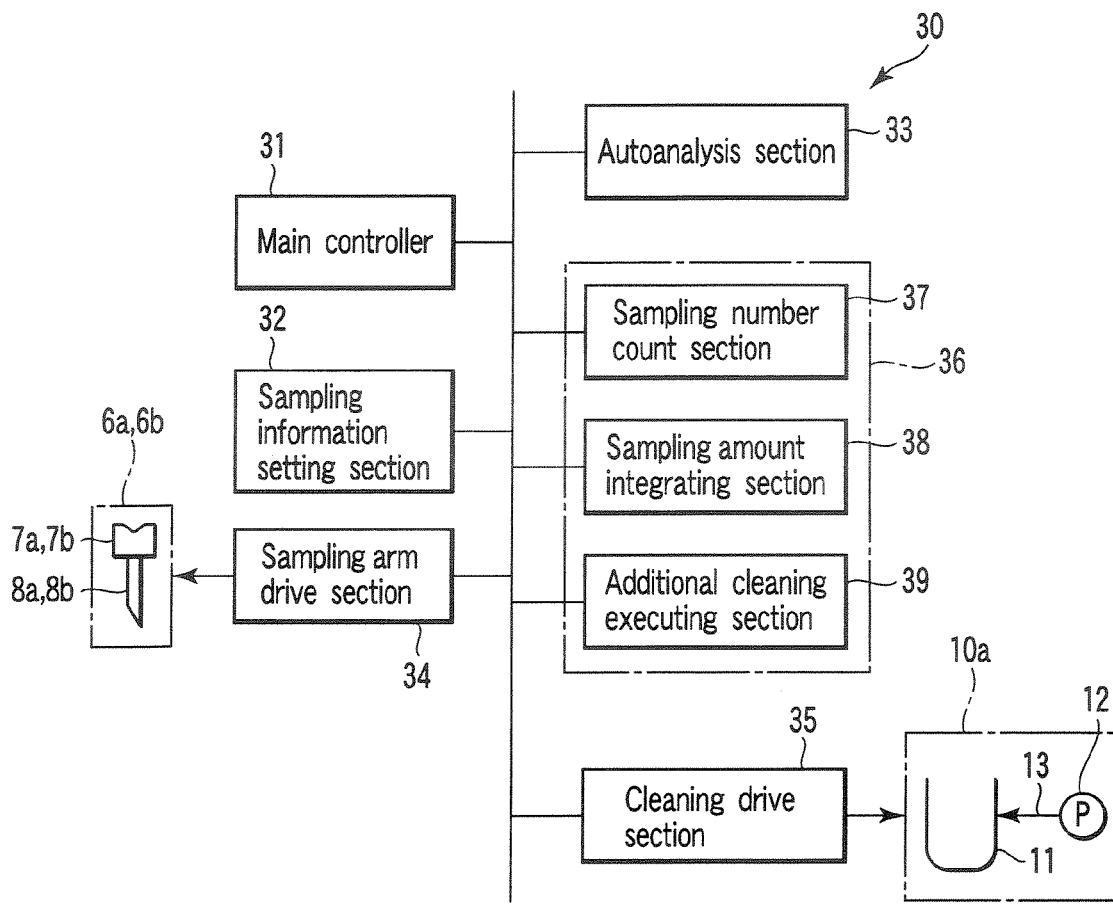
FIG. 4 is a block diagram showing a control system in the autoanalyzer.

A control system 30 will now be explained with reference to a block diagram of the control system for the autoanalyzer depicted in FIG. 4. The control system 30 is formed of a computer, and has a CPU, an RAM, an ROM, an input/output port, and others. In the control system 30, the computer executes an autoanalysis program stored in the ROM. The control system 30 has a main control section 31 formed of the CPU. The main control section 31 controls operations of an autoanalysis section 33, a sampling drive section 34, a cleaning drive section 35, and a probe cleaning adding section 36 as a probe cleaning change section in accordance with sampling information set in a sampling information setting section 32.

Information of each specimen 4 sequentially carried by the carriage unit 3 is preset in the sampling information setting section 32. Information of each specimen 4 is, e.g., a name of a patient from who the specimen 4 is taken, a type of the specimen 4, e.g., a blood serum or urine, each inspection item of the specimen 4 in the biochemical analysis unit 1 and the immunological analysis unit 2, the number of times of sampling for each of the various specimens 4 in the biochemical analysis unit 1 and the immunological analysis unit 2, a sampling amount for one time, and others.

The autoanalysis section 33 operates the biochemical analysis unit 1 in accordance with each predetermined sampling period to perform biochemical analysis of the specimen 4 divided and poured into the reaction container 9a and also carries out a regular analysis operation of operating the cleaning mechanism 9a in the biochemical analysis unit 1. The autoanalysis section 33 operates the immunological analysis unit 2 in accordance with each predetermined sampling period to effect immunological analysis of the specimen 4 divided and poured into the reaction container 9b.

The autoanalysis section 33 operates the biochemical analysis unit 1 as follows. The autoanalysis section 33 issues each operation command to the sampling drive section 34 in accordance with each of the sampling periods $T_1$ to Tn to operate the sampling mechanism 6a, thereby effecting each of sampling operations $S_1$ to Sn for the specimen 4. The autoanalysis section 33 issues each operation command to the cleaning drive section 35 in accordance with each of the sampling periods $T_1$ to Tn after each of the sampling operations $S_1$ to Sn for each specimen 4, thus performing each of cleaning operations $W_1$ to Wn for the sampling probe 8a.

Each of the sampling periods $T_1$ to Tn corresponds to an operation in one cycle of the sampling mechanism 6a mentioned above. Therefore, the respective sampling periods $T_1$ to Tn correspond to operations of the sampling mechanism 6a in n cycles.

The sampling drive section 34 operates and controls each of the sampling mechanisms 6a and 6b. The sampling drive section 34 moves, e.g., the sampling arms 7a and 7b of the respective sampling mechanisms 6a and 6b. The sampling drive section 34 performs a sucking operation and a discharge operation of the respective sampling probes 8a and 8b.

The cleaning drive section 35 operates the cleaning pump 12 to inject the cleaning liquid 13 into the cleaning tank 11.

Figure 6:
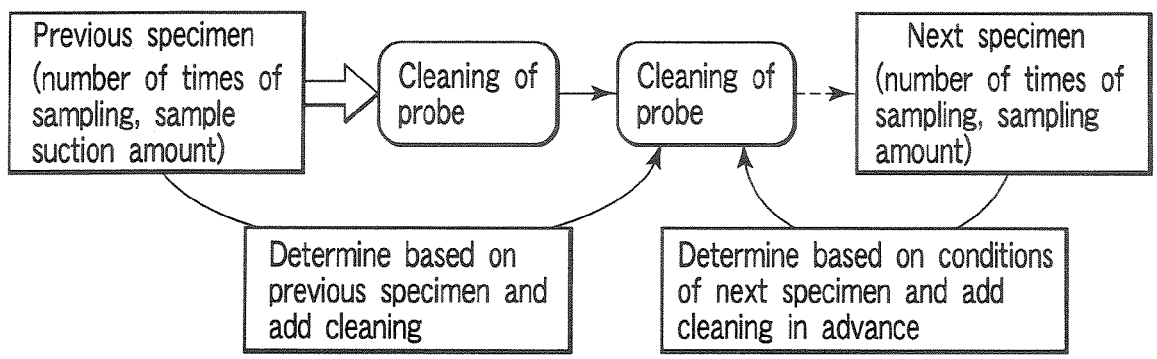
FIG. 6 is a view showing a sampling probe cleaning method in the autoanalyzer.

As shown in FIG. 6, the probe cleaning adding section 36 judges, e.g., whether the number of times of sampling of the specimen 4 by the sampling mechanism 6a exceeds a preset number of times of sampling. Further, the probe cleaning adding section 36 also judges whether a sampling integration amount of the specimen 4 exceeds a preset sampling integration amount. When the number of times of sampling exceeds the set number of times of sampling or when the sampling integration amount exceeds the set sampling integration amount as a result of the judgment, the probe cleaning adding section 36 adds cleaning of the sampling probe 8a before the next sampling of the specimen 4 besides regular cleaning of the sampling probe 8a. The probe cleaning adding section 36 carries out cleaning, e.g., twice or more.

Figure 7:
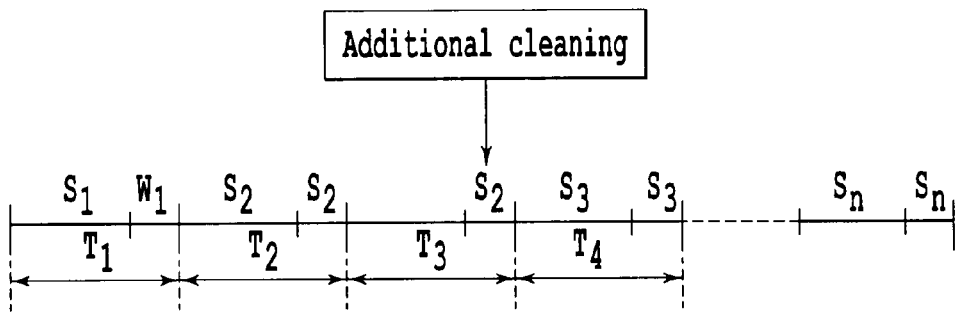
FIG. 7 is a view showing an example of a timing of additional cleaning by the autoanalyzer.

FIG. 7 shows an example of a timing of additional cleaning. The respective cleaning operations $W_1$ to Wn are regular cleaning with respect to the sampling probe 8a. When the probe cleaning adding section 36 determines that the number of times of sampling the specimen 4 by the sampling mechanism 6a exceeds the set number of times of sampling in, e.g., the sampling period $T_2$, it performs additional cleaning $W'_2$ in the next sampling period $T_3$. At this time, the probe cleaning adding section 36 cancels execution of sampling the specimen 4 and performs the additional cleaning operation $W_2'$ alone for the sampling probe 8a.

The number of times of sampling the specimen 4 is, e.g., a count value of the number of times of sampling after replacing the sampling probes 8a and 8b. It is to be noted that the number of times of sampling the specimen 4 may be a count value of the number of times of sampling from, e.g., the sampling period $T_4$ following the sampling period Tn where the previous additional cleaning is effected, i.e., the sampling period $T_3$ where the additional cleaning operation $W_2'$ is performed as shown in FIG. 7.

The sampling integration amount of the specimen 4 is, e.g., an integration value of an amount of sampling the specimen 4 after replacing the sampling probes 8a and 8b. It is to be noted that the sampling integration amount of the specimen 4 may be an integration value of sampling amounts of the specimen 4 sampled from, e.g., the sampling period $T_4$ following the sampling period Tn where previous additional cleaning is effected, i.e., the sampling period $T_3$ where the additional cleaning operation $W_2'$ is performed as shown in FIG. 7.

As shown in FIG. 6, the probe cleaning adding section 36 obtains the total number of times of sampling including the number of times of sampling the next specimen 4 that is sampled by, e.g., the sampling mechanism 6a, and judges whether the total number of times of sampling exceeds a preset number of times of sampling. Furthermore, the probe cleaning adding section 36 obtains a total sampling integration amount including a sampling integration amount of the next specimen 4 to be sampled, and judges whether the total sampling integration amount exceeds a preset sampling integration amount.

When the total number of times of sampling exceeds the set number of times of sampling or when the total sampling integration amount exceeds the set sampling integration amount as a result of the judgment, the probe cleaning adding section 36 adds cleaning for the sampling probe 8a before the next sampling of the specimen 4 besides regular cleaning for the sampling probe 8a like the above example.

For instance, as shown in FIG. 7, when the sampling mechanism 6a is used to perform the sampling operation $S_2$ and the cleaning operation $W_2$ for the sampling probe 8a in the sampling period $T_2$, the probe cleaning adding section 36 obtains the total number of times of sampling including the sampling operation $S_3$ in the next sampling period $T_3$, and judges whether the total number of times of sampling exceeds the set number of times of sampling. Moreover, as shown in FIG. 7, when the sampling mechanism 6a is used to perform the sampling operation $S_2$ and the cleaning operation $W_2$ for the sampling probe 8a in the sampling period $T_2$, the probe cleaning adding section 36 obtains a total sampling integration amount including a sampling integration amount of the specimen 4 in the next sampling period $T_3$, and judges whether the total sampling integration amount exceeds a set sampling integration amount.

When the total number of times of sampling exceeds the set number of times of sampling or when the total sampling integration amount exceeds the set sampling integration amount as a result of the judgment, the probe cleaning adding section 36 adds cleaning for the sampling probe 8a before the next sampling of the specimen 4 besides regular cleaning for the sampling probe 8a like the above example.

It is to be noted that, when the probe cleaning adding section 36 likewise determines with respect to the sampling mechanism 7b that additional cleaning $W_2'$ for the sampling probe 8b is performed in the sampling period $T_2$ following the sampling period $T_1$ after the sampling operation $S_1$ and the cleaning operation $W_1$ for the sampling probe 8b are effected in the sampling period $T_1$ as shown in FIG. 7, the probe cleaning adding section 36 carries out the additional cleaning operation $W_2'$ alone for the sampling probe 8b without executing sampling of the specimen 4 in the next sampling period $T_3$.

Specifically, the probe cleaning adding section 36 has a sampling number count section 37, a sampling amount integrating section 38, and an additional cleaning executing section 39.

The sampling number count section 37 counts, e.g., the number of times of sampling after replacing the sampling probes 8a and 8b. When the sampling probes 8a and 8b are replaced, the sampling number count section 37 adds the number of times of sampling "1" to the number of times of sampling at the end of, e.g., the sampling period $T_1$ to obtain the total number of times of sampling including the number of times in the next sampling period $T_2$. It is to be noted that the sampling number count section 37 may start counting the number of times of each sampling operation with respect to the specimen 4 by the sampling probe 8a or 8b from, e.g., the sampling period $T_4$ following the sampling period $T_3$ where the additional cleaning operation $W_2'$ shown in FIG. 7 is performed.

The sampling amount integrating section 38 sequentially integrates sampling amounts of the specimen 4 by the sampling probes 8a and 8b after, e.g., replacing the sampling probes 8a and 8b to obtain an integration amount of sampling of the specimen 4. For example, the sampling amount integrating section 38 integrates a sampling amount in the next sampling period to a sampling integration amount after replacing the sampling probes 8a and 8b to obtain a total sampling integration amount including an amount in the next sampling period. As a sampling amount in the next sampling period $T_2$, information of a sampling amount set in the sampling information setting section 32 is used. It is to be noted that the sampling amount integrating section 38 may sequentially integrate sampling amounts of the specimen 4 by the sampling probes 8a and 8b from the sampling period $T_4$ following the sampling period $T_3$ where the additional cleaning operation $W_2'$ is performed as shown in FIG. 7 to obtain a sampling integration amount of the specimen 4, for example.

The additional cleaning executing section 39 receives the number of times of sampling the specimen 4 obtained by the sampling number count section 37 and the sampling integration amount of the specimen 4 acquired by the sampling amount integrating section 38. The additional cleaning executing section 39 judges whether the number of times of sampling of the specimen 4 exceeds the set number of times of sampling. Additionally, the additional cleaning executing section 39 judges whether the sampling integration amount of the specimen 4 exceeds the set sampling integration amount.

When the number of times of sampling exceeds the set number of times of sampling or when the sampling integration amount of the specimen 4 exceeds the set sampling integration amount as a result of the judgment, the additional cleaning executing section 39 performs additional cleaning for the sampling probe 8a. When the number of times of sampling exceeds the set number of times of sampling and the sampling integration amount of the specimen 4 also exceeds the set sampling integration amount, the additional cleaning executing section 39 likewise performs additional cleaning for the sampling probe 8a.

The additional cleaning executing section 39 judges whether the total number of times of sampling including the number of times of sampling the next specimen 4 to be sampled exceeds the set number of times of sampling. Further, the additional cleaning executing section 39 judges whether the total sampling integration amount including a sampling integration amount of the next specimen 4 to be sampled exceeds the set sampling integration amount.

When the total number of times of sampling exceeds the set number of times of sampling or when the total sampling integration amount exceeds the set sampling integration amount as a result of the judgment, the additional cleaning executing section 39 carries out additional cleaning for the sampling probe 8a. When the total number of times of sampling exceeds the set number of times of sampling and the total sampling integration amount also exceeds the set sampling integration amount, the additional cleaning executing section 39 likewise performs additional cleaning for the sampling probe 8a.

Figure 8:
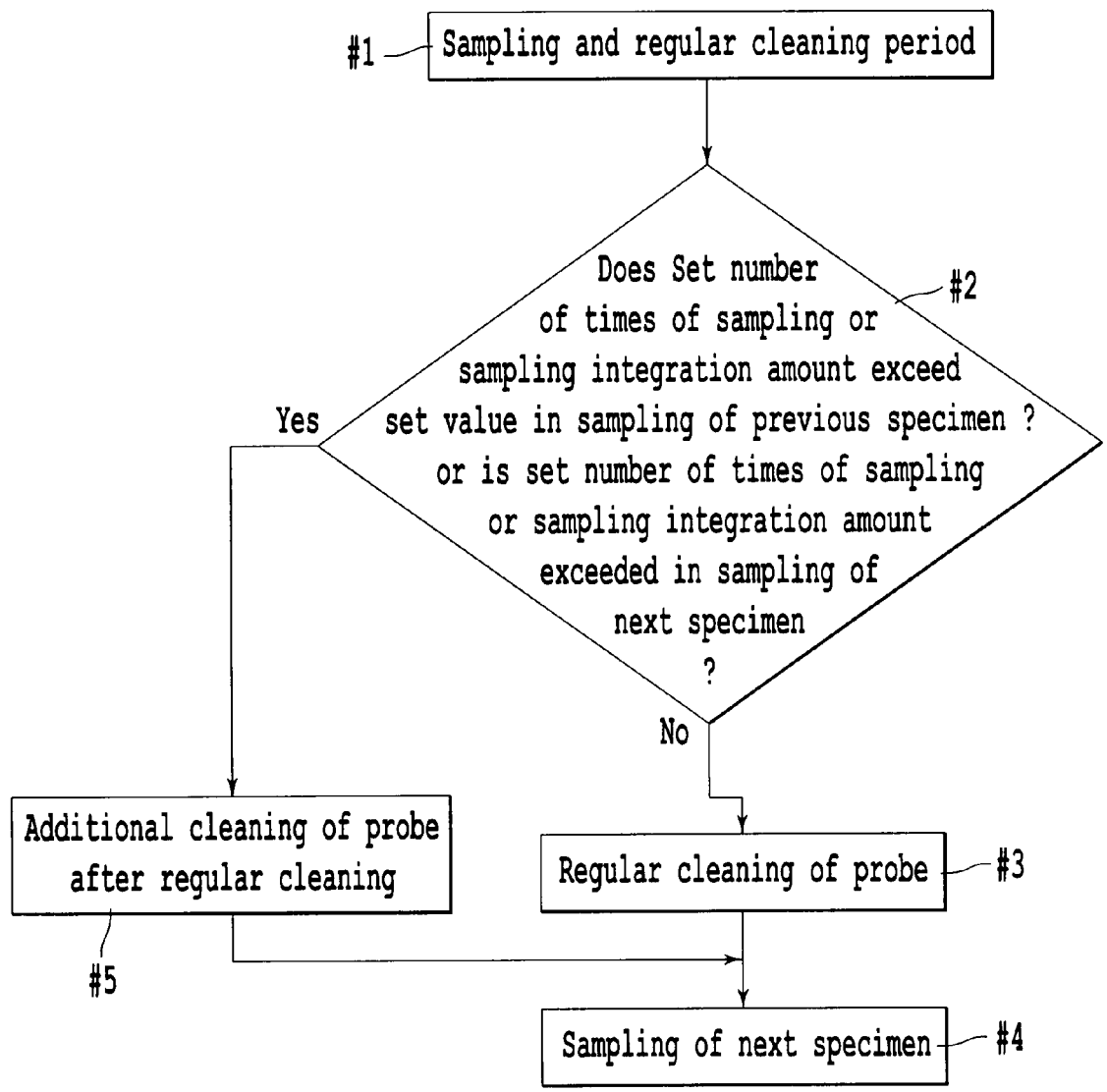
FIG. 8 is a cleaning flowchart in the autoanalyzer.

A cleaning operation in the apparatus having the above-described structure will now be explained with reference to a cleaning flowchart depicted in FIG. 8.

The specimen 4, e.g., a blood serum or urine taken from, e.g., each different patient is accommodated in each specimen container 5. Each specimen container 5 is mounted on the carriage unit 3. The carriage unit 3 sequentially carries each specimen container 5 from the biochemical analysis unit 1 to the immunological analysis unit 2.

Figure 5:
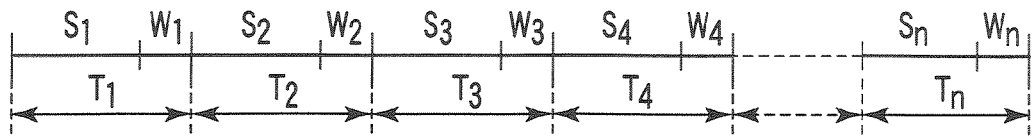
FIG. 5 is a timing chart showing a specimen sampling operation and a sampling probe cleaning operation in accordance with each sampling period in the autoanalyzer.

The main control section 31 operates and controls the autoanalysis section 33. As a result, when the specimen container 5 reaches the biochemical analysis unit 1, the autoanalysis section 33 issues each operation command to the sampling drive section 34 in accordance with each of the sampling periods $T_1$ to Tn as shown in FIG. 5, for example. Consequently, the sampling mechanism 6a performs each of the sampling operations $S_1$ to Sn in accordance with each of the sampling periods $T_1$ to Tn. At the same time, the cleaning mechanism 10a carries out each of the cleaning operations $W_1$ to Wn for the sampling probe 8a after each of the sampling operations $S_1$ to Sn in accordance with each of the sampling periods $T_1$ to Tn.

Divided pouring of each specimen 4 and the cleaning operation of the sampling probe 8a in each of the sampling periods $T_1$ to Tn (one cycle) are as follows. The sampling mechanism 6a moves the sampling probe 8a to, e.g., a position above the specimen container 5 from an installation position of the cleaning mechanism 10a. Then, the sampling mechanism 6a moves down the sampling probe 8a to be immersed in the specimen 4 in the specimen container 5, and sucks the specimen 4. Here, sampling of the specimen 4 by the sampling probe 8a is carried out in accordance with a sampling amount set n the sampling information setting section 32.

Subsequently, the sampling mechanism 6a elevates the sampling probe 8a to be moved to a position above the reaction container 9a. Then, the sampling mechanism 6a moves down the sampling probe 8a and discharges the specimen 4 into the reaction container 9a in the biochemical analysis unit 1.

Subsequently, the sampling mechanism 6a moves the sampling arm 7a to an installation position of the cleaning mechanism 10a. Here, the cleaning mechanism 10a cleans the sampling probe 8a. That is, the autoanalysis section 33 issues each operation command to the sampling drive section 34 every time each of the sampling operations $S_1$ to Sn ends. As a result, the sampling mechanism 6a inserts the sampling ram 7a into the cleaning tank 11. Then, the autoanalysis section 33 issues an operation command to the cleaning drive section 35. The cleaning pump 12 injects the cleaning liquid 13 into the cleaning tank 11. As a result, each of the cleaning operations $W_1, W_2, \ldots,$ Wn for the sampling arm 8a is carried out every time each of the sampling operations $S_1$ to Sn ends. When cleaning the sampling probe 8a is finished, the sampling mechanism 6a again moves the sampling arm 7a to the position above the specimen container 5.

The biochemical analysis unit 1 sequentially performs biochemical analysis with respect to each specimen 4 divided and poured into each reaction container.

In the biochemical analysis unit 1 and the immunological analysis unit 2, when each of the sampling operations $S_1$ to Sn is performed, the sampling number count section 37 counts the number of times of sampling after, e.g., replacing the sampling probes 8a and 8b. It is to be noted that the sampling number count section 37 counts the number of times of the respective sampling operations with respect to the specimen 4 by the sampling probes 8a and 8b from the sampling period $T_4$ following the sampling period $T_3$ where the additional cleaning operation $W_2'$ shown in FIG. 7 is effected, for example.

The sampling amount integrating section 38 sequentially integrates sampling amounts of the specimen 4 realized by the sampling probes 8a and 8b after, e.g., replacing the sampling probes 8a and 8b to obtain a sampling integration amount of the specimen 4. It is to be noted that the sampling amount integrating section 38 sequentially integrates sampling amounts of the specimen 4 realized by the sampling probes 8a and 8b from the sampling period $T_4$ following the sampling period $T_3$ where the additional cleaning operation $W_2'$ shown in FIG. 7 is effected, thereby obtaining a sampling integration amount of the specimen 4, for example.

On the other hand, the main control section 31 operates the additional cleaning executing section 39 every time each of the sampling periods $T_1$ to Tn shown in FIG. 5 ends in, e.g., the biochemical analysis unit 1 at a step #1 (a sampling and regular cleaning period). The additional cleaning executing section 39 receives the number of times of sampling operations with respect to the specimen 4 carried out by the sampling probe 8a from the sampling number count section 37 in accordance with each of the sampling periods $T_1$ to Tn.

For example, when the sampling period $T_2$ shown in FIG. 5 ends to shift to the next sampling period $T_3$, the additional cleaning executing section 39 receives the number of times of sampling until the end of the previous sampling period, i.e., the sampling period $T_2$ from the sampling number count section 37. Furthermore, when the sampling period $T_2$ ends, the additional cleaning executing section 39 receives a sampling integration amount until the end of the sampling period $T_2$ from the sampling amount integrating section 38.

Moreover, when the sampling period $T_2$ ends, the additional cleaning executing section 39 receives a total number of times of sampling obtained by adding the number of times of sampling in the next sampling period $T_3$ from the sampling number count section 37. Additionally, when the sampling period $T_2$ ends, the additional cleaning executing section 39 receives a total sampling integration amount obtained by integrating sampling amounts in the next sampling period $T_3$ from the sampling number count section 37.

Then, at a step #2, the additional cleaning executing section 39 judges whether the number of times of sampling of the specimen 4 until the end of the sampling period $T_2$ exceeds the set number of times of sampling. Further, the additional cleaning executing section 39 judges whether the sampling integration amount of the specimen 4 until the end of the sampling period $T_2$ exceeds the set sampling integration amount.

At the step #2, the additional cleaning executing section 39 judges whether the total number of times of sampling including the number of times of sampling in the next sampling period $T_3$ exceeds the set number of times of sampling when the sampling period $T_2$ ends. Furthermore, the additional cleaning executing section 39 judges whether the total sampling integration amount including the sampling integration amount in the next sampling period $T_3$ exceeds the set sampling integration amount when the sampling period $T_2$ ends.

As a result of the judgment, when the number of times of sampling of the specimen 4 does not exceed the set number of times of sampling or when the sampling integration amount of the specimen 4 does not exceed the set sampling integration amount, the main control section 31 advances to a step #3 to issue a command for regular cleaning of the probe, i.e., with no additional cleaning due to the additional cleaning executing section 39. As a result, as shown in FIG. 5, in the sampling period $T_3$, the sampling operation $S_3$ with respect to the specimen 4 and the regular cleaning operation $W_3$ for the sampling probe 8a are effected as usual.

Moreover, as a result of the judgment, the total number of times of sampling including the number of times of sampling in the next sampling period $T_3$ does not exceed the set number of times of sampling. Alternatively, the total sampling integration amount including the sampling amount in the next sampling period $T_3$ does not exceed the set sampling integration amount. In this case, the main control section 31 advances to the step #3 to issue a command for regular cleaning of the probe, i.e., with no additional cleaning due to the additional cleaning executing section 39. As a result, as shown in FIG. 5, in the sampling period $T_3$, the sampling operation $S_3$ with respect to the specimen 4 and the regular cleaning operation $W_3$ for the sampling probe 8a are carried out as usual. FIG. 5 shows the timing of regular cleanings W1-Wn when no additional cleaning (like W'2 in period T3 in FIG. 7) is performed. On the other hand, if the number of times of sampling, or the sampling integration amount exceeds the set value as noted above and in step #2 of FIG. 8, it is determined that additional cleaning is to be performed after regular cleaning as shown by W'2 in T3 of FIG. 7.

On the other hand, when the sampling period $T_2$ ends and the number of times of sampling of the specimen 4 exceeds the set number of times of sampling the main control section 31 advances to step #5 and allows the additional cleaning executing section 39 to execute additional cleaning after regular cleaning. This advancement to step #5 allowing the additional cleaning executing section 39 to execute additional cleaning after regular cleaning also occurs when the sampling integration amount of the specimen 4 exceeds the set sampling integration amount. In this case, the main control section 31 also advances to step #5 and allows the additional cleaning executing section 39 to execute additional cleaning after regular cleaning.

Likewise, when the total number of times of sampling including the number of times of the sampling operation $S_3$ in the next sampling period $T_3$ exceeds the set number of times of sampling the main control section 31 advances to step #5 as noted above and allows the additional cleaning executing section 39 to execute the above-noted additional cleaning. As noted above, this advancement to step #5 allowing the additional cleaning executing section 39 to execute additional cleaning after regular cleaning also occurs when the total sampling integration amount in the sampling period $T_3$ exceeds the set sampling integration amount. In this case, the main control section 31 also advances to step #5 and allows the additional cleaning executing section 39 to execute additional cleaning after regular cleaning.

The additional cleaning executing section 39 adds cleaning of the sampling probe 8a before the next sampling operation $S_3$ besides regular cleaning of the sampling probe 8a to execute cleaning, e.g., twice or more. For example, the probe cleaning adding section 36 performs the sampling operation $S_2$ and the cleaning operation $W_2$ for the sampling probe 8a in the sampling period $T_2$ with respect to the sampling mechanism 6a as shown in FIG. 7, and then carries out the additional cleaning operation $W_2'$ alone for the sampling probe 8a in the next sampling period $T_3$ without effecting the sampling operation $S_3$ with respect to the specimen 4.

Subsequently, the main control section 31 returns to a normal state, and performs the sampling operation $S_3$ with respect to the specimen 4 and the cleaning operation $W_3$ for the sampling probe 8a in the sampling period $T_4$ as shown in FIG. 7.

In the sampling mechanism 7b on the immunological analysis unit 2 side, likewise, when it is determined that the number of times of sampling of the specimen 4 exceeds the set number of times of sampling or that the sampling integration amount of the specimen 4 exceeds the set sampling integration amount, the main control section 31 advances to the step #5 and allows the additional cleaning executing section 39 to execute additional cleaning.

Likewise, when it is determined that the number of times of sampling with respect to the next specimen 4 to be sampled exceeds the set number of times of sampling or that the total sampling integration amount including the sampling amount in the next sampling period exceeds the set sampling integration amount, the main control section 31 advances to the step #5 and allows the additional cleaning executing section 39 to execute additional cleaning like the above example.

As explained above, according to the first embodiment, when the number of times of sampling of the specimen 4 exceeds the set number of times of sampling or the sampling integration amount of the specimen 4 exceeds the set sampling integration amount, or when the total number of times of sampling including the number of times of sampling with respect to the next specimen 4 to be sampled exceeds the set number of times of sampling or the total sampling integration amount including the sampling amount in the next sampling period exceeds the set sampling integration amount, the additional cleaning operation alone for the sampling probe 8a or 8b is carried out in the next sampling period without executing the sampling operation with respect to the specimen 4.

As a result, the sampling probe 8a or 8b can be assuredly cleaned. An amount of contamination of the sampling probe 8a or 8b can be reduced as compared with that in conventional cleaning. Even if the number of times of sampling of the specimen 4 or the sampling integration amount is increased, performance requiring carry-over between the specimens 4 can be assured.

When the total number of times of sampling including sampling in the next sampling period exceeds the set number of times of sampling or the total sampling integration amount including the sampling amount in the next sampling period exceeds the set sampling integration amount, the additional cleaning operation is carried out. As a result, the sampling probe 8a or 8b can be cleaned before performance requiring carry-over between the specimens 4 cannot be assured due to contamination of the sampling probe 8a or 8b, thus securing the performance requiring carry-over between the specimens 4.

Therefore, the biochemical analysis unit 1 and the immunological analysis unit having measurement sensitivity considerably higher than that of the biochemical analysis unit 1 can perform analysis of each specimen 4 with a high inspection accuracy.

Contamination of the sampling probe 8a or 8b is checked, e.g., once a week, once a month, or on a periodical base. The contamination check is carried out when a contamination degree of the sampling probe 8a or 8b is measured and a measurement results shows a high contamination level. According to this apparatus, since additional cleaning is carried out, performance required in carry-over between the sampling probes 8a and 8b can be assured for a long time. A burden of checking contamination of each of the sampling probes 8a and 8b can be alleviated.

Additional cleaning of each of the sampling probes 8a and 8b is performed based on an amount, an injection power, an injection time, and others of the cleaning liquid 13 which are the same as those in regular cleaning. The additional cleaning operation can be performed without changing settings of, e.g., an amount, an injection power, an injection time, and others of the cleaning liquid 13 in the cleaning mechanism 9.

A second embodiment according to the present invention will now be explained. It is to be noted that an apparatus structure according to this embodiment is the same as that shown in FIGS. 1 to 4, and hence different parts will be explained.

According to this embodiment, the same specimen 4 is divided and poured into a plurality of reaction containers 9a from one specimen container 5, for example. For instance, a sampling mechanism 6a moves a sampling probe 8a to, e.g., a position above the specimen container 5 from an installation position of a cleaning mechanism 10a, moves down the sampling probe 8a to be immersed in the specimen 4 in the specimen container 5, sucks the specimen 4, moves up the sampling probe 8a, moves the sampling probe 8a to a position above the reaction container 9a, and moves down the sampling probe 8a to discharge the specimen 4 into the reaction container 9a.

Then, the sampling mechanism 6a moves up a sampling arm 7a, again moves the sampling arm 7a to the position above the specimen container 5 that is the same as the above-described specimen container 5, immerses the sampling probe 8a in the specimen 4 in the specimen container 5, sucks the specimen 4, moves up the sampling probe 8a, moves the sampling probe 8a to, e.g., a position above a reaction container 9a that is different from the above-explained reaction container 9a, and moves down the sampling probe 8a to discharge the specimen 4 into the reaction container 9a.

The sampling mechanism 6a moves the sampling probe 8a to, e.g., an installation position of the specimen container 5 from the installation position of the cleaning mechanism 10a to be immersed in the specimen 4 in the specimen container 5, sucks the specimen 4, and discharges the sucked specimen 4 into the reaction container 9a. This operation is determined as one cycle, and this cycle is repeated more than once.

When the cycle is repeated for a preset number of times, the sampling mechanism 6a moves the sampling arm 7a to the installation position of the cleaning mechanism 10a. Here, the cleaning mechanism 10a cleans the sampling probe 8a.

A probe cleaning change section 36 judges whether additional cleaning is carried out like the first embodiment. When it is determined that additional cleaning is performed as a result of the judgment, the probe cleaning change section 36 repeats the cycle for the preset number of times, then executes a regular cleaning state, and performs cleaning of the sampling probe 8a alone without executing sampling of the specimen 4 in the next cycle.

A cleaning operation in the apparatus having the above-described structure will now be explained with reference to a cleaning flowchart of FIG. 8.

Figure 9:
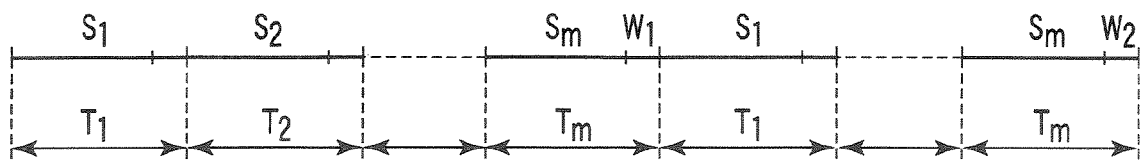
FIG. 9 is a timing chart showing a specimen sampling operation and a sampling probe cleaning operation in accordance with each sampling period in a second embodiment of an autoanalyzer according to the present invention.

When the specimen container 5 reaches a biochemical analysis unit 1, an autoanalysis section 33 issues each operation command to a sampling drive section 34 in accordance with, e.g., each of sampling periods $T_1$ to Tm as shown in FIG. 9. As a result, the sampling mechanism 6a carries out each of sampling operations $S_1$ to Sm in accordance with each of the sampling periods $T_1$ to Tm. The respective sampling operations $S_1$ to Sm are as follows.

The sampling mechanism 6a moves the sampling probe 8a to, e.g., the position above the specimen container 5 from the installation position of the cleaning mechanism 10a, and moves down the sampling probe 8a. The sampling mechanism 6a immerses the sampling probe 8a in the specimen 4 in the specimen container 5, and sucks the specimen 4. The sampling mechanism 6a elevates the sampling probe 8a, and moves the sampling probe 8a to the position above the reaction container 9a. The sampling mechanism 6a moves down the sampling probe 8a to discharge the specimen 4 into the reaction container 9a. Then, the sampling mechanism 6a moves up the sampling arm 7a, and again moves the sampling arm 7a to the position above the specimen container 5 that is the same as the above-described specimen container 5.

When the cycle is repeated for the preset number of times m, the sampling mechanism 6a moves the sampling arm 7a to the installation position of the cleaning mechanism 10a. Here, the cleaning mechanism 10a performs a cleaning operation $W_1$ with respect to the sampling probe 8a.

Thereafter, the sampling mechanism 6a repeats sampling the specimen 4.

At a step #2, an additional cleaning executing section 39 judges whether the number of times of sampling with respect to the same specimen 4 until end of the sampling period Tm exceeds a set number of times of sampling. Further, the additional cleaning executing section 39 judges whether a sampling integration amount of the same specimen 4 until end of the sampling period $T_2$ exceeds a set sampling integration amount.

At the step #2, the additional cleaning executing section 39 judges whether the total number of times of sampling including the number of times of sampling in the next sampling period $T_1$ exceeds the set number of times of sampling when, e.g., the sampling period Tm ends. Furthermore, the additional cleaning executing section 39 judges whether a total sampling integration amount including a sampling integration amount in the next sampling period $T_1$ exceeds the set sampling integration amount when the sampling period Tm ends.

Figure 10:
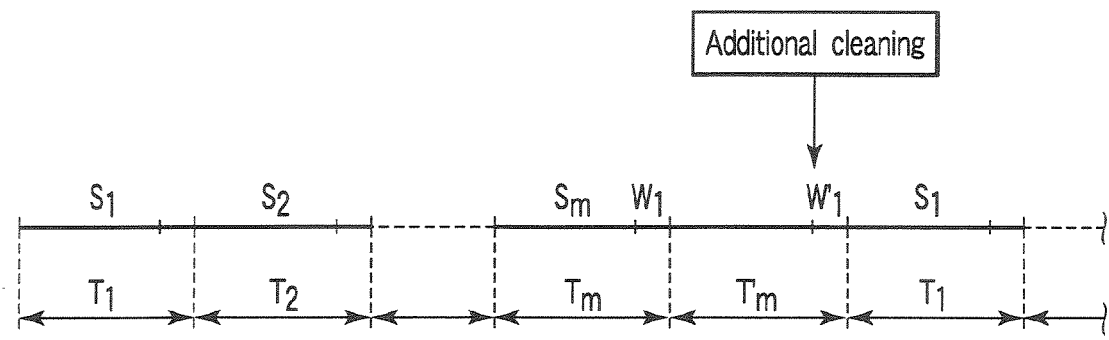
FIG. 10 is a view showing an example of a timing of additional cleaning by the autoanalyzer.

As a result of the judgment, the number of times of sampling of the specimen 4 exceeds the set number of times of sampling. Alternatively, the sampling integration amount of the specimen 4 exceeds the set sampling integration amount. In this case, a main control section 31 advances to step #3, and issues a command of performing regular cleaning (as at $W_1$ in period Tm of FIG. 10) and additional cleaning W' (as in period Tm' of FIG. 10) with respect to the additional cleaning executing section 39. Consequently, as shown in FIG. 10, in a sampling period Tm', a cleaning operation $W_1'$ for the sampling probe 8a is performed after regular cleaning $W_1$. In contrast, if it is determined in step #2 that the preset value of the number of times of sampling or the weighted sampling amount (sampling integration amount) is not exceeded, no additional cleaning is performed after the regular cleaning is completed.

In a sampling mechanism 7b on an immunological analysis unit 2 side, likewise, when it is determined that the number of times of sampling of the specimen 4 exceeds a set number of times of sampling or that a sampling integration amount of the specimen 4 exceeds a set sampling integration amount, the main control section 31 advances to a step #5 and allows the additional cleaning executing section 39 to execute additional cleaning like the above example. Likewise, when it is determined that the number of times of sampling with respect to the next specimen 4 to be sampled exceeds the set number of times of sampling or that a total sampling integration amount including a sampling amount in the next sampling period exceeds the set sampling integration amount, the main control section 31 advances to the step #5 and allows the additional cleaning executing section 39 to execute additional cleaning.

As explained above, according to the second embodiment, even if the same specimen 4 is divided and poured into, e.g., the plurality of reaction containers 9a from the single specimen container 5, the sampling probes 8a and 8b can be assuredly cleaned like the first embodiment. An amount of contamination of each sampling probe 8a or 8b can be reduced as compared with conventional cleaning. Even if the number of times of sampling or the sampling integration amount of the specimen 4 is increased, performance requiring carry-over between the specimens 4 can be assured.

A third embodiment according to the present invention will now explained. An apparatus structure according to this embodiment is the same as that shown in FIGS. 1 to 4, and hence different parts will be described.

Figure 11:
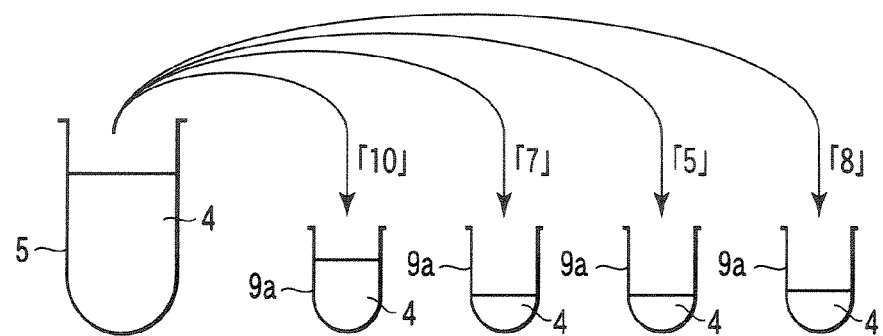
FIG. 11 is a view showing weighting with respect to each specimen sampling amount in a third embodiment of an autoanalyzer according to the present invention.

According to this embodiment, a sampling amount of a specimen 4 for each inspection item is weighted, that is it is subject to weighing. For example, and as more fully explained below, a preset contamination amount can be set at a value (e.g., "10" as noted below) and when the sampling amount is at or above this set value it is multiplied by a first weighting factor (e.g., "2" as noted below). In contrast, when the sampling amount is less than this value, it is multiplied by a second weighting factor (e.g., "1" as noted below). Thus weighting is performed to obtain a weighted sampling amount. As shown in FIG. 11, the specimen 4 accommodated in a specimen container 5 is divided and poured into a plurality of reaction containers 9a. A divided pouring amount (a sampling amount) to each reaction container 9a is, e.g., "10", "7", "5" or "8".

A sampling amount integrating section 38 weights a sampling amount that increases adhesion of contamination to a sampling probe 8a. The sampling amount integrating section 38 has a preset contamination amount, and judges whether a sampling amount for each reaction container 9a exceeds the set contamination amount for that container. When the sampling amount for a particular reaction container 9a exceeds the set contamination amount for that particular container 9a as a result of the judgment, the sampling amount integrating section 38 weights the sampling amount for that particular container 9a reaction container 9a, and uses the weighted sampling amount to obtain an integration amount of sampling of the specimen 4.

For example, the set contamination amount is set to, e.g., "10". A weighting value is set to, e.g., "multiplying by 2" when the set contamination amount "10" is exceeded. The weighting value is set to, e.g., "multiplying by 1" when the set contamination amount is not greater than "10". When obtaining a sampling integration amount with respect to each reaction container 9a shown in FIG. 11, the sampling amount integrating section 38 multiplies the sampling amount "10" by "2", and multiplies each sampling amount "7", "5", or "8" by "1". Therefore, the sampling amount integrating section 38 calculates 10×2+7×1+5×1+8×1 to obtain the sampling integration amount.

An additional cleaning executing section 39 receives the sampling integration amount from the sampling amount integrating section 38. The additional cleaning executing section 39 judges whether the sampling integration amount exceeds a preset sampling integration amount, e.g., whether the sampling integration amount exceeds a preset sampling integration amount "80". When the sampling integration amount exceeds the set sampling integration amount, the additional cleaning executing section 39 executes additional cleaning.

A cleaning operation in the apparatus having the above-described structure will now be explained.

For example, the sampling probe 8a divides and pours the specimen 4 accommodated in the specimen container 5 into the plurality of reaction containers 9a. Each sampling amount with respect to each reaction container 9a is, e.g., "10", "7", "5", or "8".

The sampling amount integrating section 38 judges whether each sampling amount "10", "7", "5", or "8" with respect to each reaction container 9a exceeds a set contamination amount "10". As a result of the judgment, since the sampling amount "10" with respect to the reaction container 9a exceeds the set contamination amount, the sampling amount integrating section 38 multiplies the sampling amount "10" with respect to the reaction container 9a by "2" to perform weighting. The sampling amount integrating section 38 multiplies each sampling amount "7", "5", or "8" with respect to each reaction container 9a by "1" to perform weighting. The sampling amount integrating section 38 calculates 10×2+7×1+5×1+8×1 to obtain a sampling integration amount "40".

The additional cleaning executing section 39 receives the sampling integration amount "40" from the sampling amount integrating section 38. The additional cleaning executing section 39 judges whether the sampling integration amount "40" exceeds a preset sampling integration amount, e.g., a preset sampling integration amount "80". When the sampling integration amount exceeds the set sampling integration amount, the additional cleaning executing section 39 executes additional cleaning.

As explained above, according to the third embodiment, the sampling amount with respect to the specimen 4 is weighted. For example, a sampling amount that increases an amount of adhesion of contamination to the sampling probe 8a is subjected to weighting using a large value, e.g., weighting of multiplying by "2", thereby obtaining a sampling integration amount. As a result, as compared with an example where a sampling integration amount is simply obtained, additional cleaning of the sampling probe 8a can be performed on an earlier stage. It is possible to securely assure performance required in carry-over between the specimens 4.

It is to be noted that the present invention is not restricted to each of the foregoing embodiments, and a probe cleaning adding section 36 may perform additional cleaning for the sampling probes 8a and 8b based on the following probe cleaning method.

When the number of times of sampling of the specimen 4 is to exceed a set number of times of sampling, a probe cleaning adding section 7 may add cleaning of the sampling probes 8a and 8b before the next sampling of the specimen 4 besides regular cleaning of the sampling probes 8a and 8b.

When a sampling integration amount of the specimen 4 is to exceed a set sampling integration amount, the probe cleaning adding section 7 may add cleaning of the sampling probes 8a and 8b before the next sampling of the specimen 4 besides regular cleaning of the sampling probes 8a and 8b.

When the total number of times of sampling including the number of times of sampling with respect to the next specimen 4 to be sampled exceeds the set number of times of sampling, the probe cleaning adding section 7 may add cleaning of the sampling probes 8a and 8b before the next sampling of the specimen 4.

When a total sampling integration amount including a sampling integration amount of the next specimen 4 to be sampled exceeds the set sampling integration amount, the probe cleaning adding section 7 may add cleaning of the sampling probes 8a and 8b before the next sampling of the specimen 4.

When at least two of the four cases where the number of times of sampling of the specimen 4 is to exceed the set number of times of sampling, where the sampling integration amount of the specimen 4 is to exceed the set sampling integration amount, where the total number of times of sampling including the number of times of sampling with respect to the next specimen 4 to be sampled exceeds the set number of times of sampling, and where the total sampling integration amount including the sampling integration amount of the next specimen 4 to be sampled exceeds the set sampling integration amount are satisfied, the probe cleaning adding section 7 may add cleaning of the sampling probes 8a and 8b before the next sampling of the specimen 4.

Figure 12:
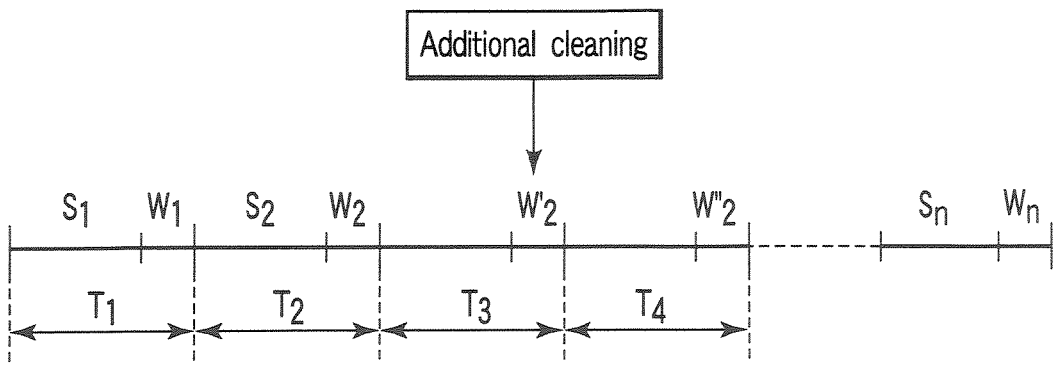
FIG. 12 is a view showing another timing of additional cleaning by the autoanalyzer according to the present invention.

The probe cleaning adding section 7 may increase the number of times of additional cleaning for the sampling probes 8a and 8b. For example, as shown in FIG. 12, in regard to additional cleaning, an additional cleaning operation $W_2'$ alone may be performed in a sampling period $T_4$ after the additional cleaning operation $W_2'$ in a sampling period $T_3$. As a result, additional cleaning is continuously performed for two cycles in the respective sampling periods $T_3$ and $T_4$.

Figure 13:
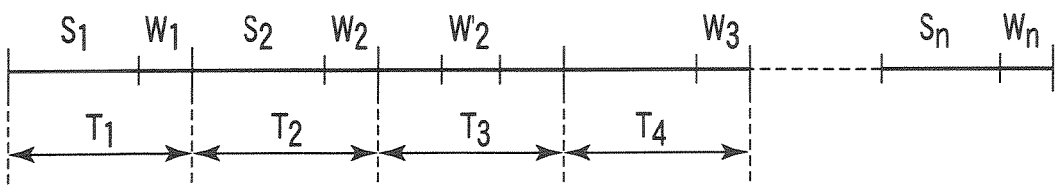
FIG. 13 is a view showing still another timing of additional cleaning by the autoanalyzer according to the present invention.

The probe cleaning adding section 7 can move a timing of additional cleaning for the sampling probes 8a and 8b in, e.g., the sampling period $T_3$. For example, as shown in FIG. 13, the additional cleaning operation $W_2'$ may be performed in the middle of the sampling period $T_3$. The additional cleaning operation $W_2'$ may be carried out in the first half of the sampling period $T_3$.

Figure 14:
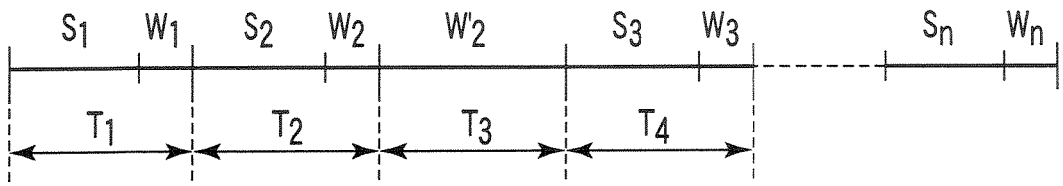
FIG. 14 is a view showing yet another timing of additional cleaning by the autoanalyzer according to the present invention.
Figure 15:
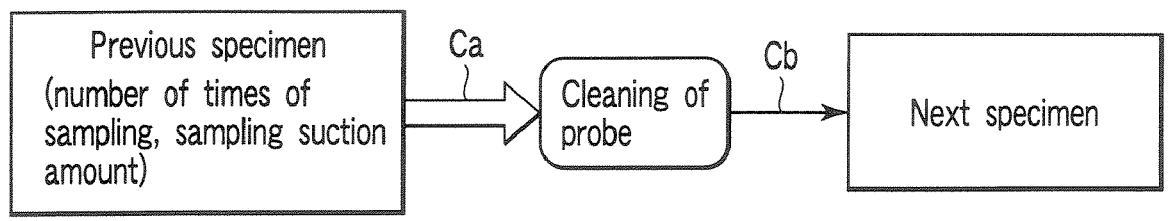
FIG. 15 is a view showing a conventional sampling probe cleaning method.

The probe cleaning adding section 7 may prolong a time required for additional cleaning of the sampling probes 8a and 8b. For example, as shown in FIG. 14, a time of the additional cleaning operation $W_2'$ may be set to an entire time in the sampling period $T_3$. Moreover, a time of the additional cleaning operation $W_2'$ may be set to an entire time of the respective sampling periods $T_3$ and $T_4$ that are continuous for two cycles.

Even when a sampling integration amount of the specimen 4 used for one of a plurality of inspection items exceeds a preset amount, the probe cleaning adding section 7 may perform the additional cleaning operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An autoanalyzer comprising:
   a probe that samples a specimen;
   an analysis unit that analyzes the specimen sampled by the probe;
   a cleaning mechanism that cleans the probe; and
   a probe cleaning change section that changes at least one of the number of times of cleaning and a cleaning time of the probe by the cleaning mechanism based on at least one of the number of times of sampling of the specimen and a sampling amount of the specimen by the probe, wherein
   the probe cleaning change section has a preset number of times of sampling, and adds cleaning of the probe when the number of times of sampling exceeds the set number of times of sampling or when the total number of times of sampling including the next sampling exceeds the set number of times of sampling.

2. An autoanalyzer comprising:
   a probe that samples a specimen;
   an analysis unit that analyzes the specimen sampled by the probe;
   a cleaning mechanism that cleans the probe; and
   a probe cleaning change section that changes at least one of the number of times of cleaning and a cleaning time of the probe by the cleaning mechanism based on at least one of the number of times of sampling of the specimen and a sampling amount of the specimen by the probe, wherein
   the probe cleaning change section has a preset sampling integration amount, and adds cleaning of the probe when the sampling integration amount exceeds the set sampling integration amount or when the total sampling integration amount including a sampling amount in the next sampling exceeds the set sampling integration amount.

3. An autoanalyzer comprising:
   a probe that samples a specimen;
   an analysis unit that analyzes the specimen sampled by the probe;
   a cleaning mechanism that cleans the probe; and
   a probe cleaning change section that changes at least one of the number of times of cleaning and a cleaning time of the probe by the cleaning mechanism based on at least one of the number of times of sampling of the specimen and a sampling amount of the specimen by the probe, wherein
   the probe cleaning change section has a preset number of times of sampling and a preset sampling integration amount, and adds cleaning of the probe when one or both a case where the number of times of sampling exceeds the set number of times of sampling and a case where the total number of times of sampling including the next sampling exceeds the set number of times of sampling are achieved and when one or both a case where the sampling integration amount exceeds the set sampling integration amount and a case where the total sampling integration amount including a sampling amount in the next sampling exceeds the set sampling integration amount are achieved.

4. The autoanalyzer according to claims 1, 2, or 3, wherein sampling the specimen by the probe and cleaning the probe are operations in one cycle, the cycle being repeated for a plurality of number of times, and the probe cleaning change section performs cleaning of the probe alone without executing sampling of the specimen by the probe in the next cycle when addition of the cleaning is determined.

5. The autoanalyzer according to claim 4, wherein the probe cleaning change section performs cleaning of the probe alone without executing sampling of the specimen by the probe in the plurality of continuous cycles including the next cycle.

6. The autoanalyzer according to claim 4, wherein the probe cleaning change section prolongs a time required for cleaning the probe in the next cycle.

7. The autoanalyzer according to claims 1, 2, or 3, further comprising:
   a plurality of specimen containers that respectively accommodate the plurality of different specimens; and
   a plurality of reaction containers into which the respective specimens are poured,
   wherein the probe repeats an operation as one cycle more than once, the operation including sampling the specimen accommodated in one of the respective specimen containers, then discharging the sampled specimen into one of the respective reaction containers, and being cleaned by the cleaning mechanism, and the probe cleaning change section performs cleaning of the probe alone without executing sampling of the specimen in the next cycle when addition of the cleaning is determined.

8. The autoanalyzer according to claims 1, 2, or 3, further comprising:
   one specimen container that accommodates the specimen; and
   a plurality of reaction containers into which the specimen is divided and poured, wherein the probe repeats an operation as one cycle more than once, divides and pours the specimen accommodated in the specimen container into the plurality of reaction containers, and is then cleaned by the cleaning mechanism after divided pouring of the specimen into the reaction containers in a cycle having a predetermined cycle number when the number of times of repetition of the cycle reaches the predetermined cycle number, the operation including sampling the specimen accommodated in the specimen container and discharging the sampled specimen into one of the respective reaction containers, and the probe cleaning change section performs cleaning of the probe alone without executing sampling of the specimen in a cycle following the cycle having the predetermined cycle number when effecting addition of the cleaning.

9. The autoanalyzer according to claim 8, wherein the probe cleaning change section performs weighting in accordance with each sampling amount with respect to the plurality of reaction containers, uses each weighted sampling amount to obtain a sampling integration amount of the specimen, and executes the additional cleaning when the sampling integration amount exceeds a preset sampling integration amount.

* * * * *